United States Patent
Dietz et al.

(10) Patent No.: US 6,800,860 B2
(45) Date of Patent: Oct. 5, 2004

(54) OPTICAL ARCHITECTURES FOR MICROVOLUME LASER-SCANNING CYTOMETERS

(75) Inventors: Louis J. Dietz, Mountain View, CA (US); Ian Walton, Mountain View, CA (US); Scott Norton, Sunnyvale, CA (US)

(73) Assignee: SurroMed, Inc., Menlo Park, CA (US)

( * ) Notice: Subject to any disclaimer, the term of this patent is extended or adjusted under 35 U.S.C. 154(b) by 0 days.

(21) Appl. No.: 10/635,917

(22) Filed: Aug. 5, 2003

(65) Prior Publication Data

US 2004/0079893 A1 Apr. 29, 2004

Related U.S. Application Data

(62) Division of application No. 09/378,259, filed on Aug. 20, 1999, now Pat. No. 6,603,537.
(60) Provisional application No. 60/097,506, filed on Aug. 21, 1998.

(51) Int. Cl.[7] .............................................. G01N 21/64
(52) U.S. Cl. ............................... 250/458.1; 250/459.1; 356/317; 356/318
(58) Field of Search .......................... 250/459.1, 458.1, 250/461.1, 461.2; 356/317, 318

(56) References Cited

U.S. PATENT DOCUMENTS

| | | | |
|---|---|---|---|
| 5,091,652 A | * 2/1992 | Mathies et al. | 250/458.1 |
| 5,127,730 A | 7/1992 | Brelje et al. | |
| 5,192,980 A | 3/1993 | Dixion et al. | |
| 5,239,178 A | 8/1993 | Derndinger et al. | |
| 5,304,810 A | 4/1994 | Amos | |
| 5,446,532 A | 8/1995 | Yamazaki | |
| 5,523,573 A | * 6/1996 | Hanninen et al. | 250/459.1 |
| 5,547,849 A | 8/1996 | Baer et al. | |
| 5,556,764 A | 9/1996 | Sizto et al. | |
| 5,578,832 A | 11/1996 | Trulson et al. | |
| 5,682,038 A | * 10/1997 | Hoffman | 250/458.1 |
| 5,726,751 A | 3/1998 | Altendorf et al. | |
| 5,736,410 A | * 4/1998 | Zarling et al. | 436/172 |
| 5,814,820 A | * 9/1998 | Dong et al. | 250/458.1 |
| 6,104,945 A | 8/2000 | Modell et al. | |
| 6,236,945 B1 | 5/2001 | Simpson et al. | |
| 6,376,843 B1 | * 4/2002 | Palo | 250/458.1 |
| 6,377,842 B1 | 4/2002 | Pogue et al. | |
| 6,388,788 B1 | 5/2002 | Harris et al. | |
| 6,646,271 B2 | * 11/2003 | Yokokawa et al. | 250/458.1 |

FOREIGN PATENT DOCUMENTS

| | | |
|---|---|---|
| DE | 197 07 227 | 8/1998 |
| EP | 0 296 136 | 12/1988 |

OTHER PUBLICATIONS

Dietz et al (1996) Cytometry 23:177–186.

Holst (1998) CCD Arrays, Camear and Displays, 2d Ed., JCD Publishing and SPIE Optical Engineering Press.

Bruchez et al. (1998) Science 281:2013.

Wright et al. (1997) Proceedings of SPIE—The International Society for Optical Engineering Ultrasensative Biochemical Diagnostics II, Feb. 10–12, San Jose, CA.

* cited by examiner

Primary Examiner—Albert Gagliardi
(74) Attorney, Agent, or Firm—Swanson & Bratschun, LLC (57) ABSTRACT

Methods and instrumentation for performing charge coupled device (CCD)-based confocal spectroscopy with a laser spot array are provided. The methods and instruments of the invention are useful in any spectroscopic application, including, but not limited to, microscopy and microvolume laser scanning cytometry (MLSC).

4 Claims, 9 Drawing Sheets

Figure 1

— · — CHIEF RAYS

Figure 9 though the aperture, fluorescence dichroic 2
OPTICAL ARCHITECTURES FOR MICROVOLUME LASER-SCANNING CYTOMETERS

PRIORITY APPLICATION DATA

This application is a divisional of U.S. patent application Ser. No. 09/378,259, filed Aug. 20, 1999, now U.S. Pat. No. 6,603,537, which claims priority from U.S. Provisional Patent Application Ser. No. 60/097,506, filed Aug. 21, 1998, entitled "Laser-scanner confocal time-resolved fluorescence spectroscopy system".

BACKGROUND OF THE INVENTION

Microvolume laser scanning cytometry (MLSC) is a method for analyzing the expression of biological markers in a biological fluid. See, e.g., U.S. Pat. Nos. 5,547,849 and 5,556,764; Dietz et al., Cytometry 23:177–186 (1996); U.S. Provisional Application No. 60/144,798, filed Jul. 21, 1999, each of which is incorporated herein by reference. A sample, such as blood, is incubated in a capillary with one or more fluorescently-labeled probes that specifically binds to particular biological markers, such as membrane proteins displayed on the surface of a blood cell. The sample is then analyzed by a MLSC instrument, which scans excitation light from a laser over the sample along one axis of the capillary, while the capillary itself is moved in an orthogonal axis by an automated stage. Fluorescent probes in the sample emit Stokes-shifted light in response to the excitation light, and this light is collected by the cytometer and used to form an image of the sample. In such images, the cells or particles that bind to the fluorescent probes can be identified and quantitated by image analysis algorithms. The resulting information on the expression of biological markers in the sample can be used for diagnostic and prognostic medical purposes.

Current laser scanning cytometers are based on the flying spot confocal laser scanner. These systems scan a laser excitation light spot in one dimension across the sample using a rotating or reciprocating mirror, such as a mirror mounted on a galvanometer. The sample is translated in a direction orthogonal to the scan direction. The collimated excitation laser light follows an epi-illumination path through the microscope objective and is focused on the sample and the mirror scan center is imaged upon the entrance pupil of the microscope objective. Emitted light from the sample is then collected by the microscope objective, and re-traces the excitation light path back to the scanning mirror where it is descanned. The emitted light passes through a dichroic filter and a long-pass filter to separate out reflected excitation light, and is then focussed onto an optical detector through an aperture. The aperture serves as a spatial filter, and reduces the amount of out-of-focus light that is introduced into the detector. The wider the aperture, the greater the depth of focus of the system. The detector generates a signal that is proportional to the intensity of the incident light. Thus, as the laser scans the sample, an image is assembled pixel-by-pixel. This optical architecture is typically referred to as confocal fluorescence detection.

In order to detect multiple fluorescence probes, the laser scanning cytometry system can also include dichroic filters that separate the emitted light into its component wavelengths. Each distinct wavelength is imaged onto a separate detector through a separate aperture. In this way, an image of the sample is assembled pixel-by-pixel for each emitted wavelength. The individual images are termed channels, and the final multi-color image is obtained by merging the individual channels.

Figure 1:
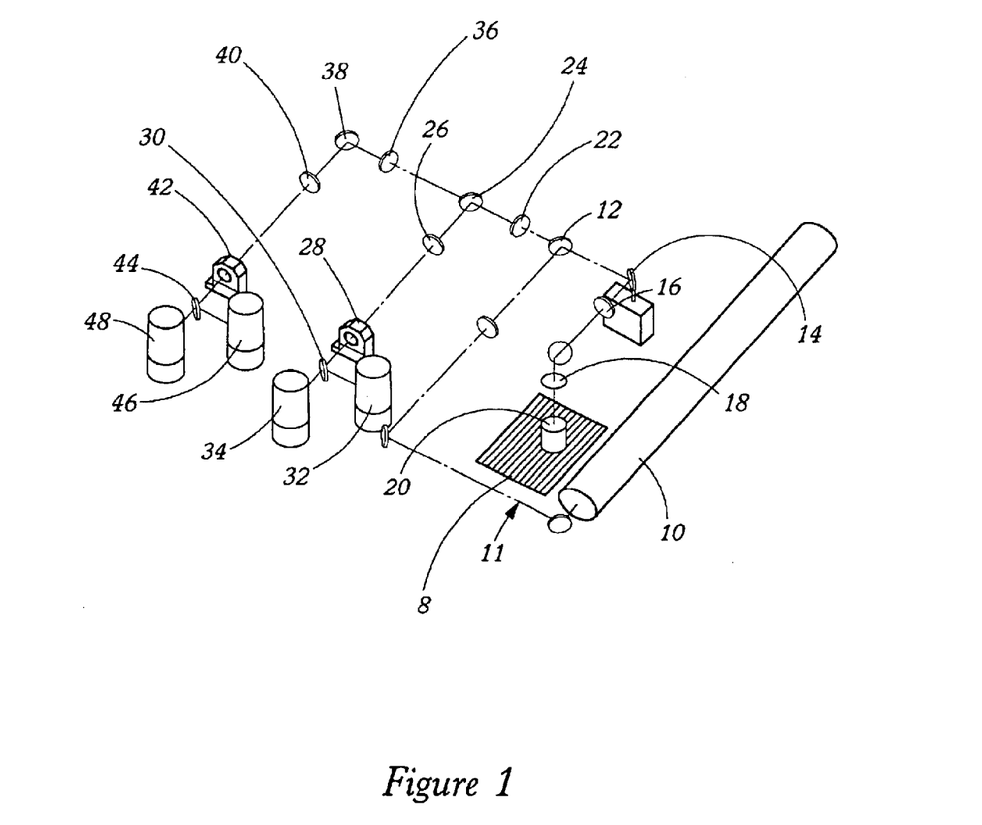
FIG. 1 illustrates a single-spot multi-channel MLSC system in which mechanical confocal apertures and photomultipliers are used. The chief ray of each ray bundle is traced.

The use of confocal 4-channel fluorescence detection for MLSC is illustrated schematically in FIG. 1, and is described in the U.S. Provisional Patent Application entitled "Improved System for Microvolume Laser Scanning Cytometry", filed Jul. 21, 1999, incorporated herein by reference in its entirety. In this embodiment, the light from a laser is scanned over a capillary array 8 wherein each capillary contains a sample that contains fluorescently-labeled species. Specifically, collimated excitation light is provided by a He—Ne laser 10. The collimated laser light is deflected by an excitation dichroic filter 12. Upon reflection, the light is incident on a galvanometer-driven scan mirror 14. The scan mirror can be rapidly oscillated over a fixed range of angles by the galvanometer e.g. ±2.5 degrees. The scanning mirror reflects the incident light into two relay lenses (relay lens 1 (16) and relay lens 2 (18)) that image the scan mirror onto the entrance pupil of the microscope objective 20. This optical configuration converts a specific scanned angle at the mirror to a specific field position at the focus of the microscope objective 20. The angular sweep is typically chosen to result in a 1 mm scan width at the objective's focus. The relationship between the scan angle and the field position is essentially linear in this configuration and over this range of angles. Furthermore the microscope objective 20 focuses the incoming collimated beam to a spot at the objective's focus plane. The spot diameter, which sets the optical resolution, is determined by the diameter of the collimated beam and the focal length of the objective. Fluorescence samples placed in a capillary array 8 in the path of the swept excitation beam emit stokes-shifted light. This light is collected by the objective 20 and collimated. This collimated light emerges from the two relay lenses (16 and 18) still collimated and impinges upon the scan mirror 14 which reflects and descans it. The stokes-shifted light then passes through an excitation dichroic filter 12 (most excitation light reflected within the optics to this point is reflected by this dichroic filter) and then through long pass filter 1 (22) that further serves to filter out any reflected excitation light. Fluorescence dichroic filter 1 (24) then divides the two bluest fluorescence colors from the two reddest. The two bluest colors are then focussed through focusing lens 1 (26) onto aperture 1 (28) in order to significantly reduce any out-of-focus fluorescence signal. After passing though the aperture, fluorescence dichroic 2 (30) further separates the individual blue colors from one another. The individual blue colors are then parsed to two separate photomultipliers 1 (32) and 2 (34). After being divided from the two bluest colors by fluorescence dichroic 1 (24), the two reddest colors are passed through long pass filter 2 (36) and reflected off a mirror (38) through focusing lens 2 (40) onto aperture 42. After passing through aperture 2, the reddest colors are separated from one another by fluorescence dichroic 3 (44). The individual red colors are then parsed to photomultipliers 3 (46) and 4 (48). In this way, four separate fluorescence signals can be simultaneously transmitted from the sample held in the capillary to individual photomultiplier light detectors (PMT1–4). Each photomultiplier generates an electronic current in response to the incoming fluorescence photon flux. These individual currents are converted to separate voltages by one or more preamplifiers in the detection electronics. The voltages are sampled at regular intervals by an analog to digitial converter in order to determine pixel intensity values for the scanned image.

Other ways are known in the art for obtaining multi-channel information in the microscopy context. For example, it is known in the art to use fluorophores that emit light with overlapping emission spectra but with different time constants of emission. Time-resolved microscopy systems typically use very fast laser pulses and high speed detection circuitry to resolve, in the time-domain, the nanosecond-scale time signatures of the fluorophores. Alternatively, the measurement can be accomplished in the frequency domain with amplitude-modulated laser sources and detection circuitry that measures phase shift and modulation amplitudes. Both of these techniques add significant complexity to the fluorescent measurement system.

Typical MLSC instruments use photomultiplier tubes (PMTs) as light detectors. PMTs are cost-effective and have high data read-out rates which allow the sample to be scanned swiftly. However, a major drawback of the PMT is its low quantum efficiency. For example, in the red to near infrared region of the electromagnetic spectrum, PMTs have quantum efficiencies of less than 10%, i.e., less than one photon in ten that impacts the PMT is actually detected.

In order to have high sensitivity and high measurement speed, it is desirable to use high power laser sources. For each fluorophore, there is a proportional relationship between the intensity of the excitation illumination and the intensity of the emitted light. This proportionality only applies up to the point at which the fluorophore is saturated. At this point, the ground state of the fluorophore is essentially depleted, and all fluorophores exist in the excited electronic configuration. Increasing laser power beyond the saturation point does not increase the intensity of the emitted light. This effect is especially pronounced with fluorophores that have long fluorescent lifetimes, such as inorganic fluorophores, and for quantum dot nanocrystals. These molecules saturate at relatively low power densities because of their long time constants of fluorescence emission. Other undesired processes can occur at higher laser power, including photodestruction and intersystem crossing. In many applications, it is desirable to operate at power densities somewhat below saturation.

In an attempt to increase the speed with which confocal images can be acquired, microscope systems have been developed in which a continuous line of laser excitation light is scanned across the sample, rather than a single spot. The line of emitted light that is produced by the sample in response to the excitation is imaged onto a slit shaped aperture. Since light is distributed over a line of pixels speed limitations due to fluorophore photo-physics are avoided. However, the depth of field, or change in lateral resolution with focus depth, of the line scanner is inversely proportional to the numerical aperture of the objective. MLSC applications require a large depth of field to accurately image cells in a deep blood suspension. High sensitivity and speed require a high numerical aperture lens but would result in a prohibitively small depth of field. This tradeoff ultimately results in limited speed and sensitivity.

Given the limitations using a PMT as a light detector, much research is currently directed towards developing higher efficiency detectors that will allow rapid image acquisition at below-saturation power densities. One such light detector is the charge coupled device (CCD). See, e.g., G. Holst, CCD Arrays, Camera and Displays, 2d Ed., JCD Publishing and SPIE Optical Engineering Press 1998. The CCD consists of an interlinked array of sensitive photodetectors, each of which can have a quantum efficiency of greater than 80%. Despite their high efficiency, CCDs are not ideal for use in the MLSC context. One reason is that the CCD is usually employed as an imaging device in which the entire field of view is excited and the CCD captures all of the emitted light in the field of view. Used in this way the depth of field and sensitivity are coupled just as in a line scanner. Furthermore, the full field illumination and collection means a substantial amount out of focus light is excited and received by the CCD detector. Even if a CCD is used in non-imaging mode in combination with a scanned laser spot and a pinhole aperture—much in the same way as a PMT is used—additional problems are encountered. Firstly, when replacing PMTs with CCDs for simultaneous multi-channel image acquisition, a separate CCD is required for each channel. The cost of providing a separate high-efficiency CCD for each channel adds greatly to the cost of the instrument. Moreover, CCDs take significantly longer to read out than PMTs, thereby placing a significant limitation on the speed with which data can be acquired.

The present invention is directed towards optical architectures for spectroscopy which can acquire data with greater speed than prior art systems. The instruments of the invention can also be used for time resolved measurements of fluorophore emission. The methods and instruments of the invention are useful in any application where spectroscopic data from a sample is required. In preferred embodiments, the methods and instruments of the invention are used for MLSC.

The invention uses CCDs in which binning is used to subdivide a single CCD into pixel groupings that collect data simultaneously from a number of different regions of a sample. Preferred embodiments of the invention use multiple laser excitation spots in combination with CCD light detectors. In some embodiments, the individual bins are further subdivided to provide spectral information for each region of the sample. The pixel intensity values for each bin are assembled by computer to give seamless images of the sample in each channel.

SUMMARY OF THE INVENTION

Two issues typically limit the speed and sensitivity performance of prior art systems. Firstly, commonly used PMT detectors have low quantum efficiencies, especially in the red to near infrared region of the optical spectrum. Secondly, these systems typically scan a focused laser spot to excite fluorescent emission in the sample. For high sensitivity and measurement speed, it is desirable to use a high power density excitation source. However, beyond certain saturating power densities (power per unit area of the laser spot), the excitation source saturates the fluorescent labels, preventing further improvement in sensitivity and measurement speed.

The preferred embodiment of the present invention uses CCD detectors (instead of PMTs) as non-imaging light-detecting devices in a confocal scanning architecture, where an array of laser spots is scanned across the sample, instead of a single spot. Two features of this invention solve the limitations described above. Firstly, the high power laser excitation is divided into multiple spots, thus reducing the power density in each spot and minimizing sensitivity and laser power limitations due to fluorophore saturation. Secondly, the CCD is used in a non-imaging mode, by defining multiple effective confocal apertures as "binned" regions of pixels on the 2 dimensional surface of the device. Each binned region is matched to an excitation laser spot which is focused into the sample. This architecture retains the controllable depth of field of a PMT-based confocal spot scanner, but also takes advantage of the very high quantum efficiencies available with CCD detectors.

BRIEF DESCRIPTION OF THE DRAWINGS

Note, that in all the drawings, the optical pathways are illustrated schematically. Angles and dimensions are not to scale.

DETAILED DESCRIPTION OF THE PREFERRED EMBODIMENTS

The present invention provides spectroscopy methods and instrumentation with a number of novel optical configurations that allow multichannel images to be acquired quickly, and/or with time-resolution of the individual fluorophore emissions. In preferred embodiments, the invention uses CCDs as light detectors, wherein groups of pixels on the CCD form bins that are imaged onto the sample by the scanning optics. In preferred embodiments, each bin functions as a confocal aperture. The size of the bin determines the width of the cone of emitted light that is detected, and hence the greater the bin size, the greater the depth of field. Light that falls on the CCD outside of the bin is not detected. Hence, each bin functions in the same way as a mechanical confocal aperture. In preferred embodiments, the invention uses an array of laser spots to scan the sample simultaneously in multiple locations. Emitted light from each spot is imaged onto a separate confocal CCD bin, and the image is built by fusing the separate images from each spot together. In other embodiments, a series of bins are imaged onto the sample at different times following excitation such that each bin on the CCD represents a different emission time, thereby enabling time-resolved fluorescence measurements to be made. The advantage of using CCD bins as confocal apertures is that re-configuration of the instrument is performed simply by changing the size and position of the bins on the CCD, rather than by any mechanical operation. The advantage of using multiple spots is that lower laser power is present at each spot in comparison to a single spot system. The lower laser power density minimizes fluorophore saturation, but total system throughput is maintained by simultaneously detecting the emission from multiple excitation spots.

Note, that in all the embodiments that follow, the methods and instrumentation of the instant invention are described in the context of MLSC. Those of skill in the art will understand, however, that the methods and instruments of the invention are useful in any spectroscopy or cytometry application, including microscopy applications. In addition, although a fluorescence imaging application is described, this scanning system can be applied to many light scatter detection modes. Examples of such possible modes include: luminescence, phosphorescence, Raman scattering, Ralyeigh scattering and Mie scattering.

Multiple Laser Spot Excitation System with Binned CCD Light Detection

In one embodiment of the invention, a laser excitation beam is converted into an array of beams, by a device such as a Damann grating. Alternatively, other spot generating devices may be used, such as a microlens array or a fiber bundle. The system is not limited to the use of a linear array of spots and can function with a two dimensional array of spots. This could allow a greater area of a CCD detector area to be used and thus enhance readout performance. Other embodiments of the device might not use a single laser beam excitation source, but rather a laser diode array, thereby omitting the requirement for a separate beam generator device. The source of the beam is imaged, with relay lenses, onto the center of the scanning mirror device, such as a galvanometer. Other embodiments of the present device include the use of other beam deflection methods. Such methods include, but are not limited to, a piezoelectric scanner, polygonal mirrors, acousto-optic deflectors, and hologons. In the present embodiment, the scan center of the galvanometer is in turn imaged by a second set of relay lenses into the entrance pupil of a microscope objective. The laser beam array is thus focused by the objective into an array of spots in the focal plane of the objective. Each spot in the array scans and excites a separate region of a sample, which sample is moved at constant velocity along the axis orthogonal to the laser spot scan axis. Fluorescent light that is emitted by the sample is collected by the objective lens, passes through a dichroic filter and is imaged onto the surface of a CCD detector that has been electronically divided into a bin of pixels of the desired size. Emitted light that impinges the CCD outside of the bin is not detected; hence the bin functions as a confocal aperture in which the confocal depth of focus can be controlled simply by changing the bin dimensions. The greater the area of the bin, the greater the depth of focus.

The multi-spot system can be used for multichannel imaging by dividing the fluorescent emission into individual wavelengths—using, for example, dichroic filters—and then directing each component wavelength to a separate CCD detector. In this embodiment, a different CCD is used for each channel, but the bin configuration for each CCD is identical. The CCDs are periodically read out in synchrony to maintain proper registration of the individual color images. Hence, this embodiment provides a multichannel MLSC instrument in which the confocal depth of focus is computer-controlled (by changing the bin dimensions), rather than being mechanically-controlled (by changing the size of a confocal aperture).

Figure 2:
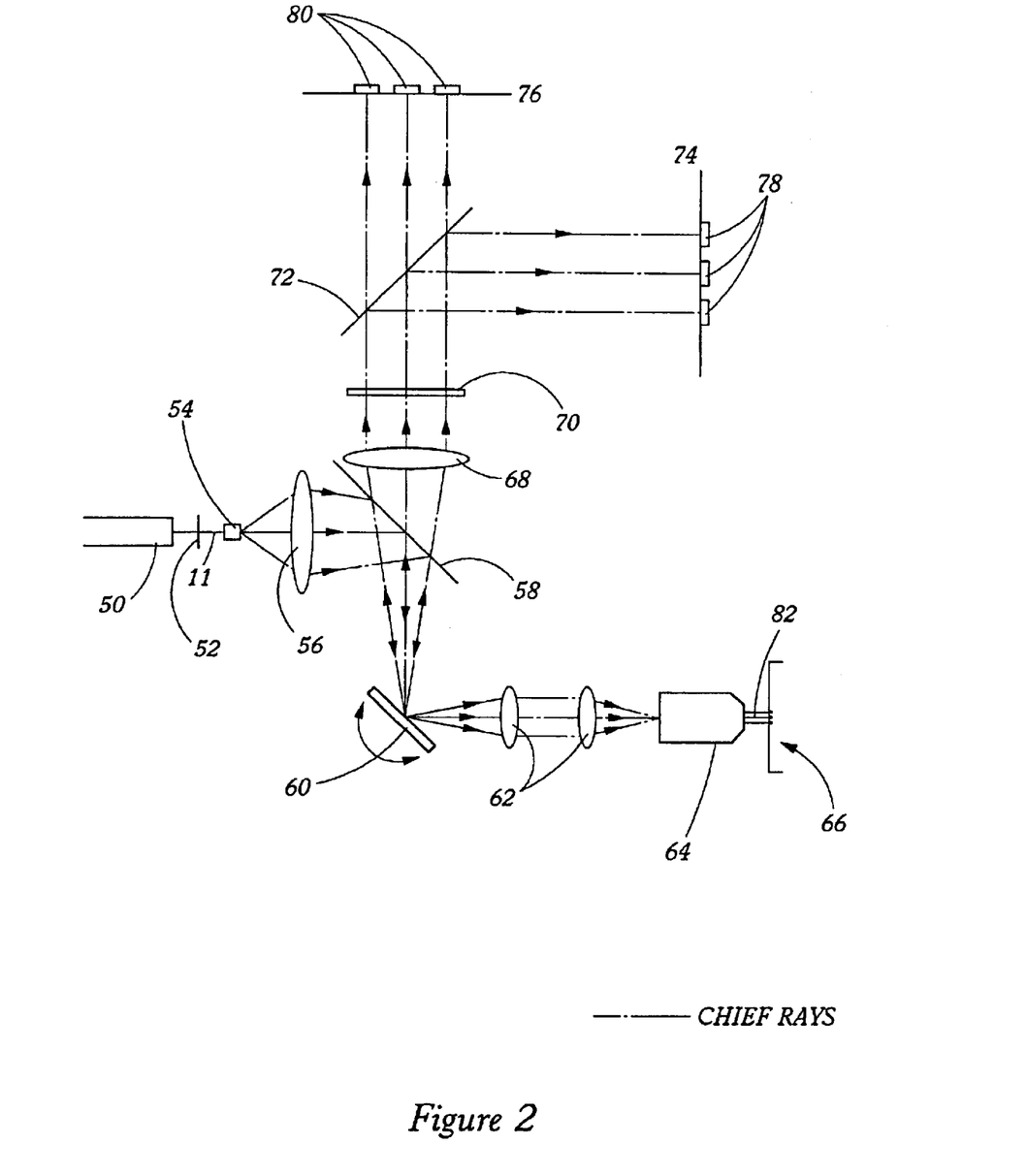
FIG. 2 illustrates a 2-channel spectroscopy system in which a sample is scanned with 3 laser excitation spots, and the resulting emission light is imaged onto CCD light detectors that have been partitioned into three confocal bins. The chief ray of each ray bundle is traced.
Figure 3:
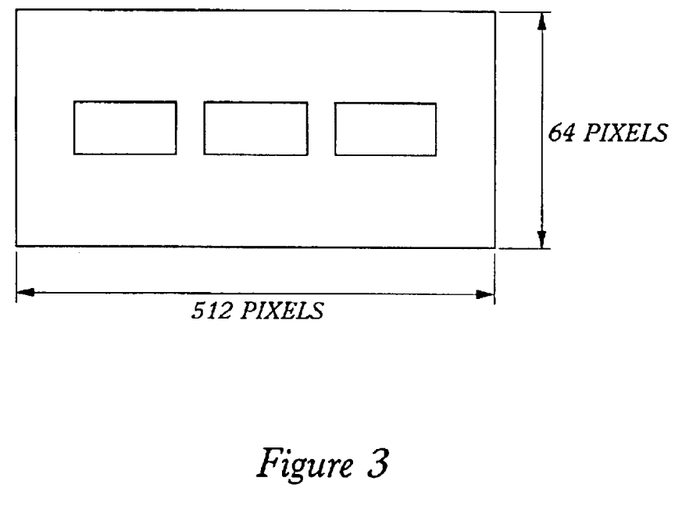
FIG. 3 illustrates a 512×64 pixel CCD detector that is partitioned into three rectangular confocal bins.

FIG. 2 illustrates one embodiment of the invention where 3 laser excitation spots are generated, then reflected off an excitation dichroic onto a galvanometer scan mirror. (In this FIG. 3 spots are chosen to illustrate the invention for convenience sake. As described below, the present invention includes any system with more than one spot.) Specifically, excitation light 11 provided by a laser 50, is passed through a laser line filter 52 and a multiple beam generating optic 54, generating three laser excitation spots. The three laser excitation spots are then passed through a lens 56 and an excitation dichroic 58 and are reflected by a galvonometer scanning mirror. The scanning spots then pass through relay lenses (62) to the entrance pupil of a microscope objective (64), and are focussed onto the sample (66) (scanned into the page). Emission light from the sample (three emission rays) is collected by the microscope objective (64), and retraces the path of the excitation spots back to the dichroic filter (58). The emission light passes through the excitation dichroic 58, a focus lens 68 and a long-pass filter, and is separated into two wavelength portions by an emission dichroic filter 72. The two portions are then imaged by a focus lens onto separate CCDs, (CCD 1 (74) and CCD 2 (76)) wherein each CCD is partitioned into three confocal bins 78 and 80. A schematic illustration of a 512×64 pixel CCD detector that is partitioned into three rectangular confocal bins is provided in FIG. 3.

Figure 4A:
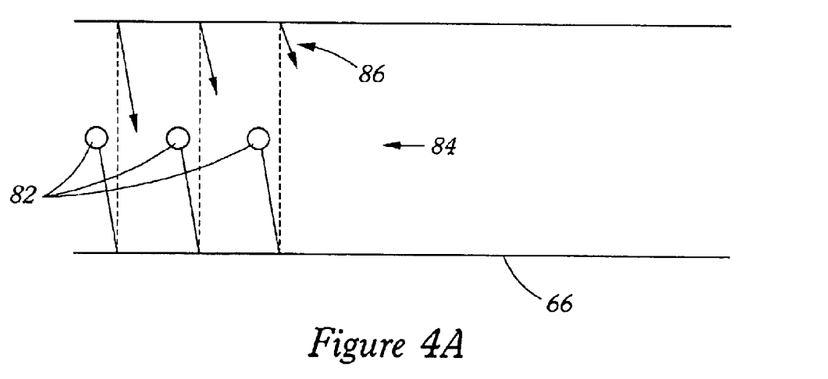
FIG. 4 illustrates the relative motion of three laser excitation spots as they are scanned over a moving sample.
Figure 4B:
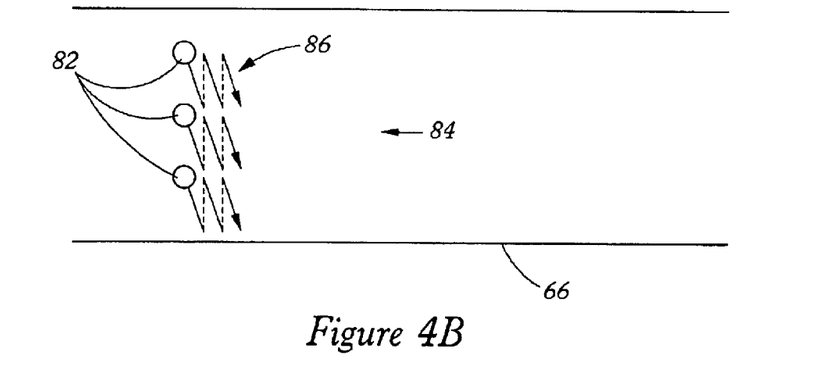

In preferred embodiments, the linear array of laser spots 82 excites emission from the sample 66. The scanning mirror device 60 rotates scanning the laser spots in the direction that is parallel to the line defined by the array of spots. The total scan deflection of each spot is chosen such that each spot scans across a length of the sample that is approximately the same length as the distance between the spots. The sample is moved along the orthogonal axis to the laser spot scan axis 84. This is illustrated schematically in FIG. 4A, where three spots scan in the vertical axis and the sample is moved horizontally. Hence, the relative spot motion traces a sawtooth pattern 86. As the spot array is scanned across the sample by the scanning mirror device, the CCD bins are periodically read out. The timing of this read out operation determines the pixel size in the scan dimension. Alternatively (FIG. 4B), the three spots 82 are arrayed orthogonal to the sample movement 84. The spots are scanned 86 across the complete sample 66. When one spot reaches the start scan position of the next spot, the sample is shuttled so that the first spot starts scanning again at the previous stop position of the last spot.

As the scan proceeds, each laser spot generates a 2-D image that is acquired by the corresponding bin of the CCD detector. The images from each spot either do not overlap, or overlap only slightly. When the scan is complete, the individual images can be joined together by a computer to provide a single seamless image.

Any number of spots can be used in the instant invention. The advantage of using multiple spots is that lower laser power density is applied to each spot, minimizing fluorophore saturation. For example, each spot in a 10 spot array has $\frac{1}{10}^{th}$ the power density of the laser spot in a single spot system using laser sources of equal power. However, each spot dwells 10 times longer in any region of the sample than the single spot system, so that the total photon flux per image pixel is the same. Since all 10 spots are excited and detected in parallel, the total scan time for a sample is the same in either case. However, by using CCDs as light detectors, significant enhancements in sensitivity result. A CCD can have at least 3 times greater quantum efficiency as a PMT; moreover using a lower excitation power density can give a significant increase in sensitivity due to the avoidance of saturation, photo-destruction and other nonlinear process excitation. Thus, the multispot system with CCD detection can be 6 to 10 times more sensitive than a single spot PMT system operating at the same scan speed. This increased sensitivity can be exploited to shorten the scan time, so a multispot system can yield comparable images to a single spot system, but in significantly less time. Alternatively, the multispot CCD system can operate at the same scan rate as the single spot system, but will be able to detect emission intensities that a conventional PMT single spot system could not detect at that scan rate. An even further advantage of using low laser power densities is that it allows the use of fluorophores that saturate at comparatively low power densities, such as inorganic fluorophores or quantum dot nanocrystals with long emission time constants.

The limit on the number of spots is determined by the required axial response of the system and the amount of cross talk between spots that can be tolerated. The more spots in the array, the more closely spaced are the confocal bins on the CCD. Axial response is proportional to bin size and so will be effectively reduced. Furthermore, the closer bins means light rejected from one bin will impinge upon another ultimately reducing system sensitivity. The present invention includes any system with more than one spot. Preferably there will be between 2 and 1000 spots and more preferably between 5 and 400.

Using CCD bins as confocal apertures is a substantial advance due to the relative simplicity of changing the dimensions of the confocal depth of field. Mechanical confocal apertures in focused light systems are typically only several $\mu m$ in diameter, and so require sophisticated and precise mechanical systems to control the aperture size. By contrast, a CCD bin can be changed simply by reconfiguring the CCD array using a computer.

The use of a CCD in MLSC is a significant improvement over prior art MLSC instruments that use PMT for light detection. The biological fluids that are assayed by MLSC auto-fluoresce and can absorb or scatter excitation light. The use of fluorophores that are excited by red light (such as the 633 nm line from a HeNe laser) reduces these problems and allows MLSC assays to be performed in whole blood. However, PMTs have a quantum efficiency of less than 10% in the red portion of the electromagnetic spectrum, leading to poor sensitivity when these fluorophores are used. By contrast, many types of CCDs have quantum efficiencies of greater than 80% in the same region of the spectrum.

As mentioned previously, current CCD detectors have a lower data read-out rate than PMTs. If a single spot is scanned over a sample and the emitted light imaged onto a CCD, the CCD would have to be read out sequentially for every single pixel in the image. By contrast, the multispot system provided by the instant invention can simultaneously acquire data for X pixels, where X is the number of spots. Thus, a 10 spot system provides data for 10 pixels in the image at each read-out event, whereas a single-spot system provides data for just a single pixel at each read-out event. Hence, the multispot system of the instant invention allows the benefits of enhanced sensitivity provided by the CCD to be achieved while minimizing the problems associated with the low data read out rate of CCDs. CCDs with higher read out rates will likely be available in the future. Using such improved CCDs will further increase the sensitivity and speed of the instruments and methods of the instant invention.

Note that all of the embodiments of the present invention can use conventional PMTs as the light detectors, rather than CCDs. In these embodiments, conventional confocal apertures are required to give the required rejection of out of focus fluoroescence. The apertures would be arranged in a pattern identical to the laser spot array.

Multiple Laser Spot Excitation System with Spectral Analysis on a Single CCD

In certain embodiments, a single CCD is used for multichannel imaging of a sample. In these embodiments, a line of laser spots is scanned over the sample, and emitted light is imaged, as described above, onto a line of confocal apertures. The layout of the array of apertures parallels the layout of the array of laser spots, such that the emitted light from each laser spot passes through a different aperture. After passing through the aperture, each beam of emitted light may be passed through dispersal optics that spread out the component wavelengths. Suitable wavelength dispersing optics include, but are not limited to, echelle gratings, holographic concave gratings, transmission gratings, or prisms. In addition, particular wavelengths can be directed mechanically onto the detector with the use of a constant deviation dispersion prism, such as the Pellin-Broca prism, or through the use of a resonant grating filter. Electro-optic methods to select wavelengths include the use of an acoustic-optic tunable filter or electro-optic resonant grating filter. The dispersal optics also image each aperture onto a separate rectangular region of a CCD so that the light that passes through each aperture is spectrally-spread along the long axis of a single rectangle. Each rectangular region on the single CCD is subdivided into bins along its long axis so that each bin collects a different wavelength of the spread light. For example, for 4-color fluorescent detection, each rectangle can be subdivided into 4 spectral bins along its long axis. Hence, each rectangular region on the CCD can essentially perform spectral analysis of the light emitted in response to excitation by a particular spot.

In a preferred system for this embodiment, the sample is scanned with a line of laser spots, and all the emitted light from the sample is imaged onto a single rectangular "slit" confocal aperture that is parallel to the line of laser spots. The emitted light then passes into dispersal optics that spectrally-spread each emitted light beam into its component wavelengths. The axis of dispersion is orthogonal to the long axis of the confocal "slit". The dispersal optics also image the component wavelengths from each emission spot onto a separate rectangular CCD region, wherein the long axis of each CCD rectangle is parallel to the axis along which the dispersal optics spread the emission spot. Consequently, the long axis of each CCD rectangle is orthogonal to the long axis of the "slit" aperture. Each rectangular region is subdivided along its long axis into spectral bins such that each of the spectral bins collects a different wavelength of light resulting from the dispersal of a single emission spot. The rectangular regions of the CCD function as a second "slit" confocal aperture oriented in the opposite dimension to the mechanical "slit" aperture. As a result, the final image is confocal in both dimensions. The depth of focus in this system can be controlled by coordinately varying the width of the mechanical "slit" aperture and the width of each CCD rectangle.

Figure 5:
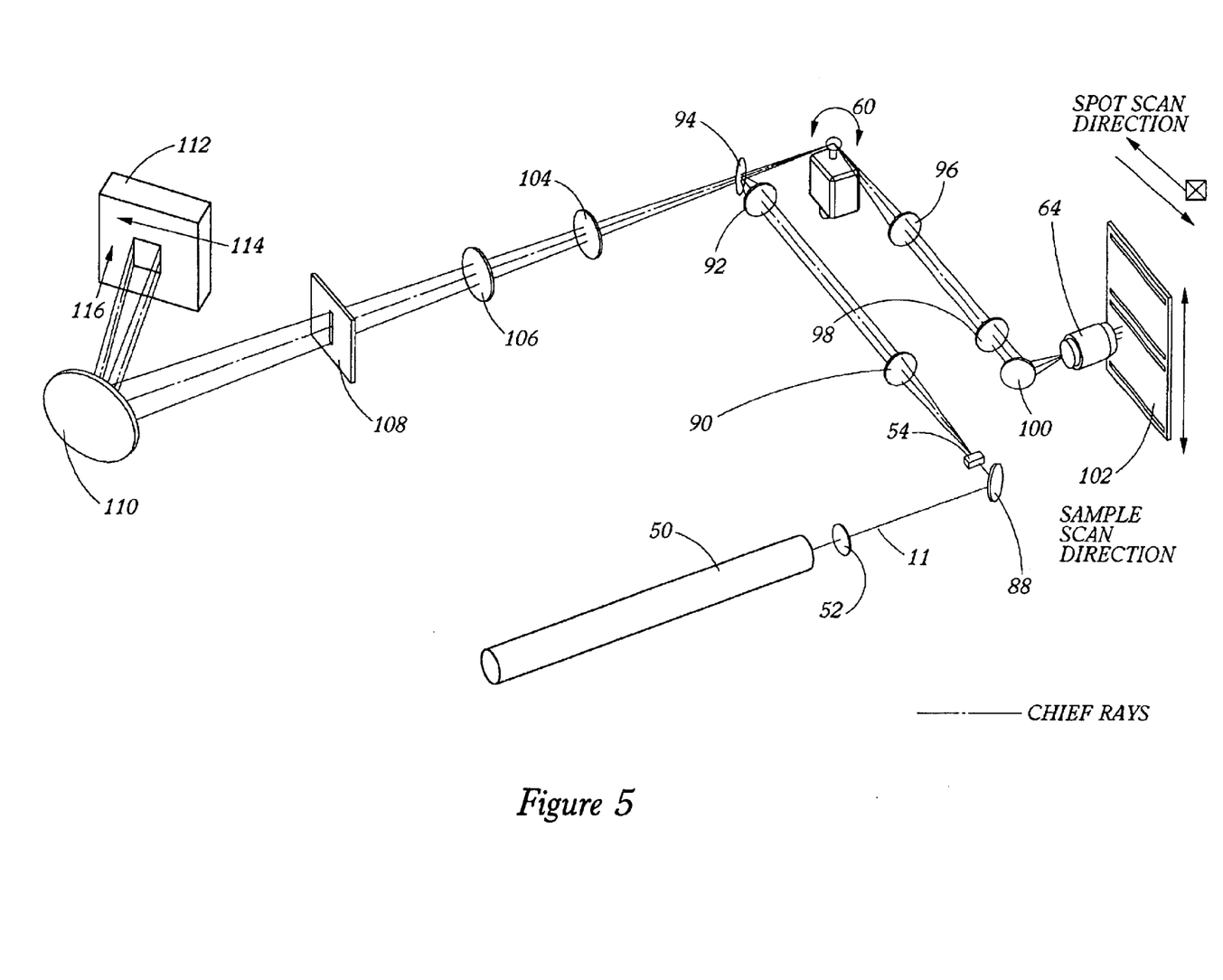
FIG. 5 illustrates one embodiment for performing multispot, multichannel confocal spectroscopy using a single CCD and a confocal slit aperture. The chief ray of each ray bundle is traced.

FIG. 5 illustrates schematically one embodiment using a slit aperture and a concave grating for wavelength dispersal. In this illustration, laser light 11 generated by laser 50 is passed through laser line filter 52 and reflected onto the spot generating optics 54—by mirror 1 (88)—. Three laser spots are generated by spot generating optics, passed by fan relay lense 1 (90) and 2 (92) to a dichroic filter 94, which dichroic reflects the laser spots on a scanning galvanometer mirror (60). The spots are then passed by galvo relay lense 1 (96) and 2 (98) to mirror 2 (100), so they re-converge at the entrance pupil of the microscope objective 64. The objective focuses the spots onto the sample 102 and the light emitted from the three spots is collected by the objective 64. The emission light rays re-trace the path of the laser spots to the dichroic filter 94. The emission light passes through the dichroic, followed by aperture lens 104 which focuses the light at the slit aperture. The focused light passes through a long pass filter 106, and then through a confocal slit aperture 108 that is oriented with the long axis of the slit parallel to the vertical axis. Emission light rays that pass through the slit aperture then fall on a concave grating 110 that re-images the spots and wavelengths onto the detector 112. In this illustration, each emission light ray is spread into multiple wavelengths along the horizontal axis. Thus, the horizontal axis of the CCD provides spectral 114 information about each emitted light ray, and the vertical axis provides spatial information 116. The spot scan direction is depicted by a double arrow 118 and the sample scan direction is depicted by a single arrow 120.

Figure 6:
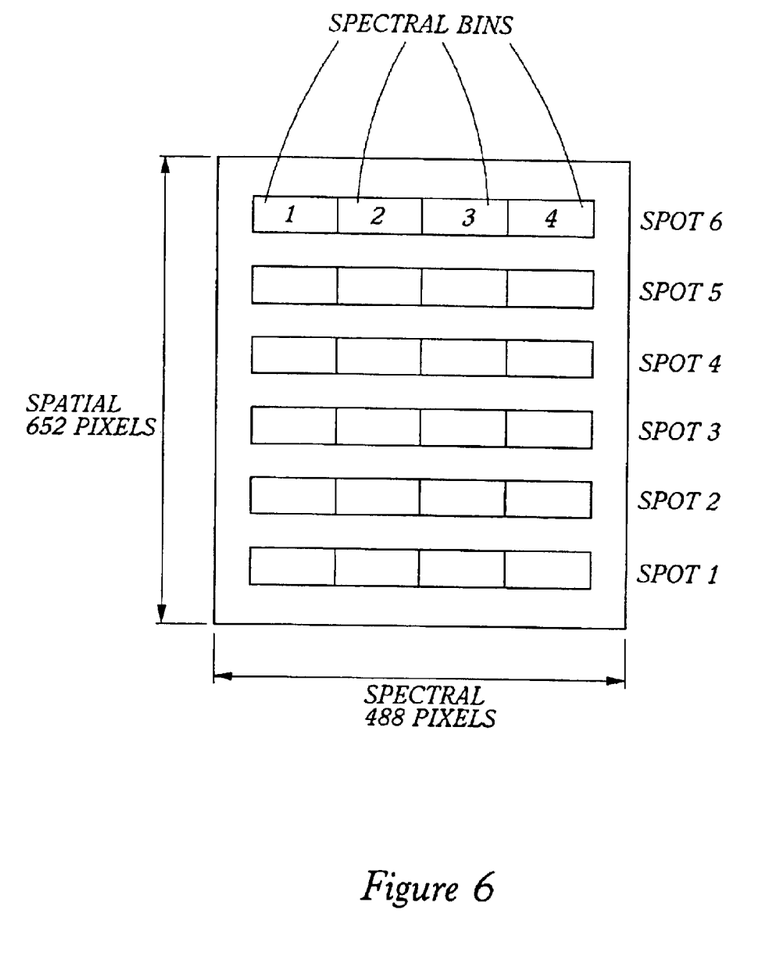
FIG. 6 illustrates schematically a 625 pixels×488 pixels CCD light detector that has been configured for a 6 spot system with 4 spectral channels.

FIG. 6 illustrates schematically a 625 pixels×488 pixels CCD light detector that has been configured for a 6 spot system with 4 spectral channels. The CCD is divided into 6 rectangular regions, and each region is subdivided into 4 spectral bins. As in FIG. 5, the horizontal axis of this CCD provides spectral information, and the vertical axis provides spatial information when used in combination with a vertically-oriented confocal slit aperture. The height of each rectangle in FIG. 6 can be adjusted to vary the confocality of the image in the horizontal axis. A suitable CCD for this application is the Pluto™ CCD from Pixelvision.

As described above, previous attempts to use line illumination in MLSC have not yielded the desired speed and sensitivity improvement because of the interaction of collection numerical aperture and system depth of field. The instant invention provides for the first time a method for distributing excitation light over an area larger than a single spot while maintaining the depth of field and axial response of a single flying spot confocal laser scanner. This is accomplished by: a) scanning the sample with individual spots of excitation light rather than a continuous line of light; and b) using a CCD bin confocal apertures, with each bin corresponding to an excitation spot.

This embodiment is also mechanically simpler than the embodiment above in which a line of pinhole apertures is used. Changing the size and orientation of a single slit aperture is simpler than changing the size of a series of comparatively smaller pinhole apertures. Thus, this embodiment retains the true two-dimensional confocality of the pinhole aperture architecture, while also possessing the mechanical simplicity of the confocal slit architecture.

An additional advantage of performing spectral analysis on the CCD in the manner outlined above is that the CCD binning in the spectral dimension can be controlled electronically. Each detection color can be optimized for the specific assay that is to be performed. This also eliminates the need in the detection system for many dichroic filters, which can vary from unit-to-unit and with temperature and humidity.

An even further advantage of using the CCD systems outlined above is that alignment of the mechanical confocal apertures with the CCD can be easily accomplished electronically. Rather than physically moving the apertures, the position of the bins on the CCD can be adjusted in order to insure that each bin is in perfect registration with its corresponding aperture. This process can be automated using, for example, a test slide containing all the fluorescent labels that are to be used in the assay.

Figure 9:
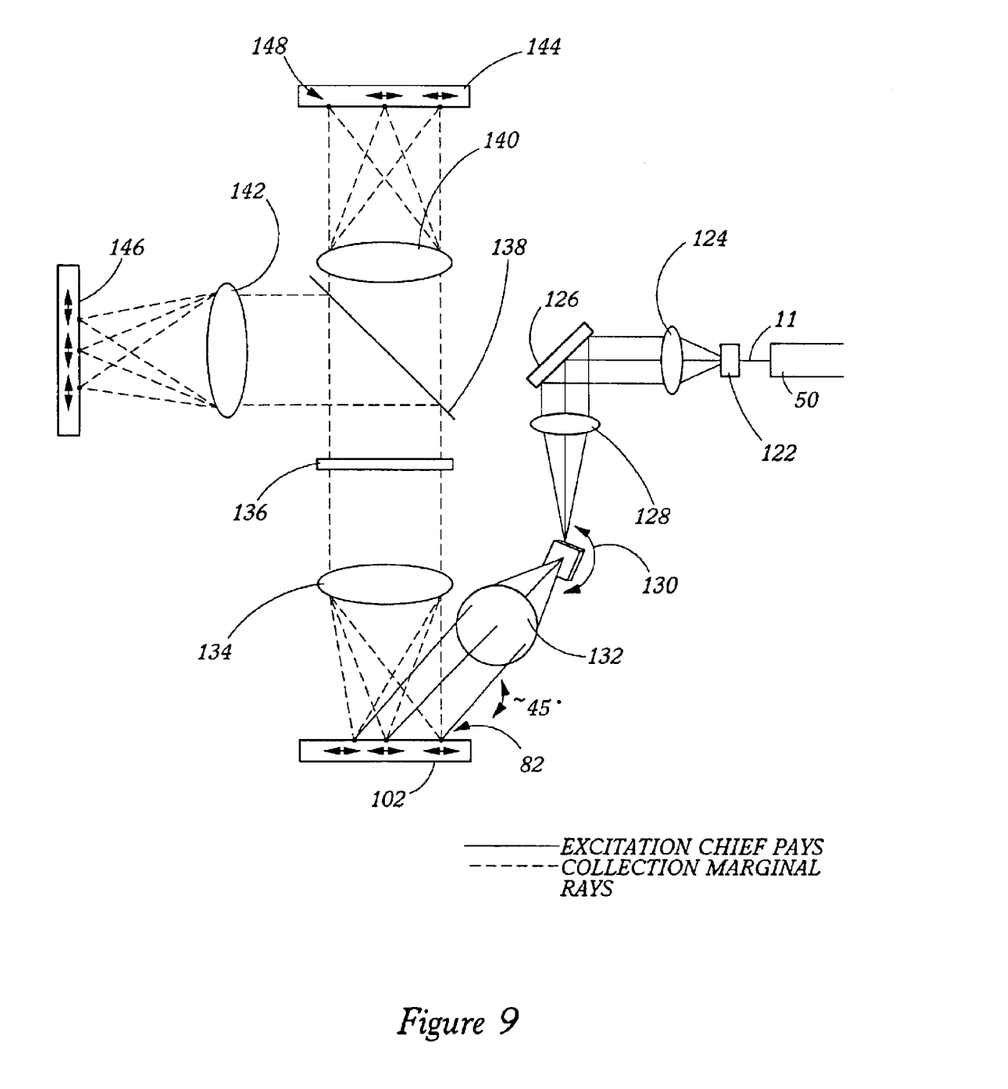
FIG. 9 illustrates schematically a non epi-illuminated spot scanner system.

In further embodiments of this invention, it is possible to use non epi-illumination of the sample. In this embodiment, illustrated in FIG. 9, the excitation light 11 generated by laser 50 is brought to the sample without passing through the collection objective. This method is referred to as off-axis illumination. See, e.g., U.S. Pat. No. 5,578,832. As in epi-illumination a fan of laser beams is generated. Possible multiple beam generating optics 122 include but are not limited to Damann and other gratings, fiber optic bundles, micro-mirror arrays, acousto-optic and electro-optic devices. The fan of rays are collected by the first fan lens 124 and re-converged on a scanning device such as a reciprocating mirror 126 with a second fan lens 128. The rays then pass through a scanning mirror 130 and a final lens 132 such that each spot 82 is focused on the sample 102 (As depicted in this Figure, the sample is scanned out of the page.). The final lens is configured such that the excitation beams are at approximately 45 degrees to the sample. Emitted light is then collected by the collection objective 134 and re-imaged on the CCD detector with a tube lens. Unwanted excitation light is eliminated with a long pass blocking filter 136. The emitted light is separated into two wavelength portions by a dichromic filter. The two portions are then passed through a lens (tube lens 1 (140) and tube lens 2 (124)) onto separate array detectors (array detector 1 (144) and array detector 2 (146)). If the spots are not de-scanned then the scanned spots will move on the detector, however the correct CCD bins can be chosen so that the readout follows the spots 148. Alternatively, the collected rays can pass via a second reciprocating device such as a mirror, in sync with the excitation mirror, to de-scan the spots. A number of different array detectors can be used to collect discrete wavelengths where the wavelengths are selected by optical filters, e.g. a dichroic filter. As in epi-illumination a dispersive element can be used to spread wavelengths over the array detector orthogonal to the spots.

Despite the extra complications involved in de-scanning the spots, off-axis has some advantages over epi-illumination. No excitation dichroic filter is needed and so many different excitation wavelengths can be used without having to change filters. Furthermore, extreme excitation wavelengths, i.e. ultraviolet or infrared, that are incompatible with collection optics can be used. Examples of reporters that use these wavelengths are: 2 photon up converting phosphors that use 980 nm excitation and emit in the visible region; and nanocrystals that are optimally excited in the UV, <400 nm, but emit in the visible regions. See, e.g., Bruchez et al., Science 281:2013 (1998); Wright, W. H. et al., Proceedings of SPIE—The International Society for Optical Engineering Ultrasensitive Biochemical Diagnostics II Feb. 10–Feb. 12, 1997 v 2985 1997 San Jose, Calif., USA.

All embodiments of the invention described above include system designs where the regions of the sample illuminated by the spot array are imaged by an optical system onto the surface of a CCD detector. Alternative system embodiments use mechanical apertures to provide the necessary confocal apertures, with non-imaging optical systems, such as fiber optics or fiber bundles, to transfer light passed through the apertures to the surface of the detector. Thus the system designer can choose the optimal spatial mappings between the excitation spot array and the detector surface. This allows the designer to choose from a wider variety of detector devices, or to more efficiently utilize the surface area of the device. For example, if the excitation spot array consists of a linear array of spots, a linear array of apertures could be used to collect the emitted light from the sample passing the light into optical fibers, with one fiber or fiber bundle per aperture. The outputs of the multiple fibers or fiber bundles could be arranged, for example, into a square-shaped 2-dimensional array, and imaged, directly or through dispersing optics, onto the surface of the detector. In this manner the designer can provide a better match to the form factor of a given CCD device, or fill up the surface of a CCD with more spots than could be utilized with imaging optics only.

Time-Resolved Spectroscopy Systems

The methods of the present invention can also be used to perform time-resolved MLSC. As described above, in time-resolved fluorescence microscopy, images of the sample are taken at predetermined time intervals after excitation illumination. This allows observation of multiple fluorophores with different emission time constants. In the present invention, time-resolved images can be obtained by imaging a series of confocal CCD bin apertures over the sample at predetermined times behind the laser excitation spot(s). The confocal bins are scanned over the sample by the same optical system that scans the laser spot. The physical separation between CCD bins maps into a difference in emission time for the sample. The time separation is a function of the scan velocity across the sample.

Figure 7:
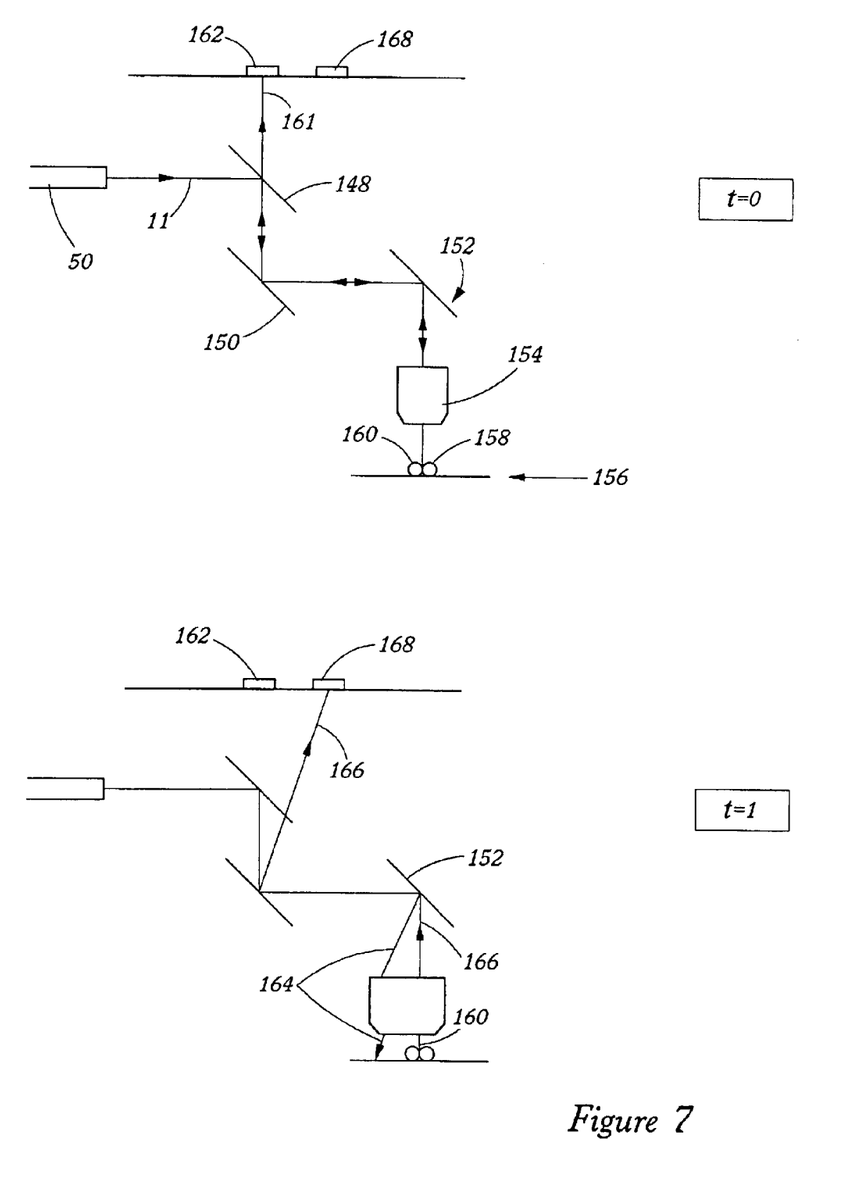
FIG. 7 illustrates a time-resolved confocal spectroscopy system in which a binned CCD collects the emission light at predetermined times following laser spot excitation.

Such a system can function as follows in one embodiment illustrated schematically in FIG. 7. Specifically, excitation light 11 provided by a laser 50, is passed through a dichroic filter 148 and reflected by a mirror 150 and a galvanometer scanning mirror 152 to the entrance pupil of a microscopic objective 154. At t=0, the laser spot excites a first region of the sample 156 in which fluorophore F1 158 and F2 160 are present. F1 has an emission time constant such that the fluorescence emitted from F1 is practically coincident with excitation. Hence, light from F1 retraces 161 the path of the laser beam, passes through a dichroic filter 148, and is imaged onto CCD confocal bin B1 162. At t=1, the scanning mirror has deflected, and a second region of the sample is receiving excitation illumination 164. Also at t=1, F2 which was excited in the first region of the sample at t=0 emits. Because the scan mirror has deflected between between t=0 and t=1, the light path followed by F2 emission is not coincident with the laser path. As a result, the fluorescence from F2 follows a path that is displaced by a predetermined amount relative to fluorescence from F1. Light from F2 can be collected by a separate confocal bin, B2 168, on the CCD. It will be understood that additional bins can be defined on the CCD in order to obtain additional time intervals. The distance between the bins (at constant scan speed) determines the time interval between each fluorescence measurement event.

In other embodiments, a multispot excitation array as described above is used for time resolved measurements. In this embodiment, the CCD is divided into a matrix of bins. In one dimension, the bins provide positional information for the emitted light. In the other dimension, the bins provide time-resolved fluorescence measurements. For example, a system for performing three time-resolved measurements for each 10 excitation laser spots would comprise a 10×3 array of CCD bins. The dimensions of each bin can be independently varied in order to optimize detection for particular fluorophores.

Figure 8:
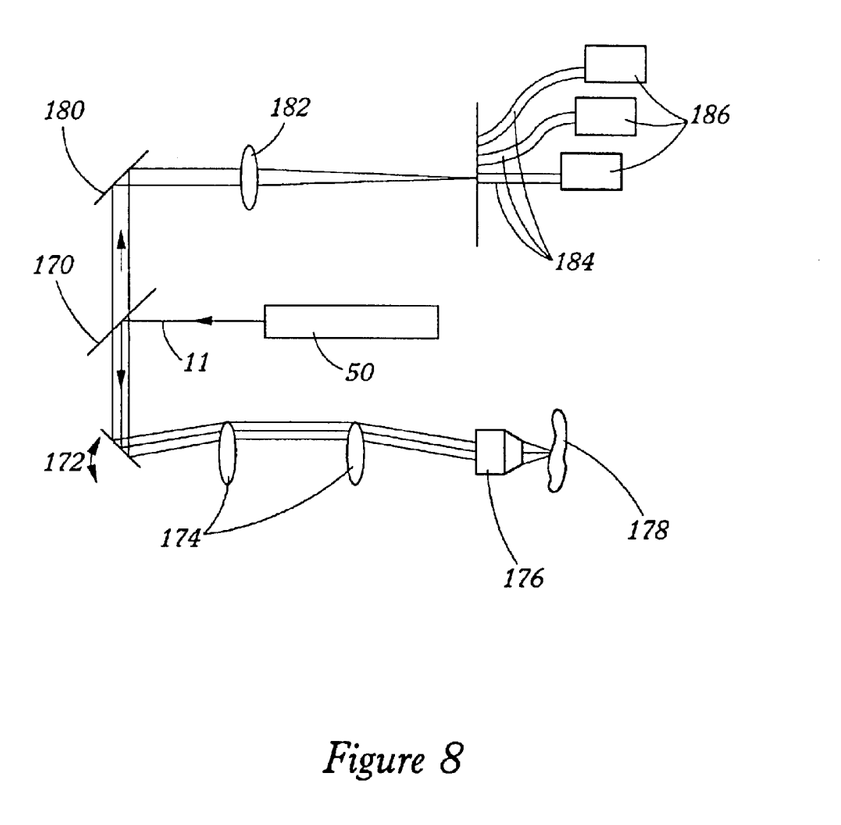
FIG. 8 illustrates a time-resolved confocal spectroscopy system in which multiple optical fibers act as confocal apertures that are imaged over the sample at predetermined times after laser spot excitation.

In other embodiments, time-resolved spectroscopy is performed using multiple pinhole confocal apertures implemented with optical fibers 184 operatively coupled to light detection devices 186. The spacing between the confocal apertures determines the time intervals for the fluorescence measurement events. As in the embodiment involving CCD bins, the individual pinhole confocal apertures are scanned over a particular region of the sample at different times after excitation of that region. As an alternative to pinhole apertures, this embodiment can be performed using optical fibers. The core of each fiber acts as a pinhole, and the light transmitted through the fibers is delivered to multiple PMTs. As before, the spacing between the illuminated end of the optical fibers determines the time interval between each fluorescence measurement. This embodiment is illustrated schematically in FIG. 8. Excitation light 11, provided by laser 50, is passed through a dichroic filter 170, reflected off of a scanning mirror 172, through relay lenses 174 to an objective lens 176 and focused onto the sample 178. The emission light is reflected by a mirror 180, passes through a focusing lens 182 and then through the multiple pinhole confocal apertures 184 onto PMT detectors 186.

In still further embodiments, time resolved fluorescence spectroscopy is performed in tandem with emission wavelength spectroscopy of the light emitted at each time interval. In certain embodiments, this is done using a series of pinhole apertures that are imaged over the sample as described above at different times behind a single laser excitation spot. Emission light that passes through each aperture is then passed through dispersal optics—such as a concave diffraction grating or a prism—that speed the emitted light into its component wavelengths. The component wavelengths from each time interval are then imaged by the dispersal optics onto a separate rectangular region of a CCD, wherein the long axis of the rectangle is parallel to the axis along which the emitted light was spread. Each pinhole aperture is mapped to a separate rectangular region on the CCD. The individual rectangles are subdivided along their long axes into spectral bins, and the spread light from each aperture falls onto those bins in a wavelength-dependent manner.

In even further embodiments, the invention provides a method for performing mutispot time-resolved fluorescence spectroscopy in tandem with fluorescence emission wavelength spectroscopy. This system functions in the same way as the multispot system with a confocal slit architecture, as described above. However, in order to perform time-resolved measurements, the system has a series of slit apertures that are imaged over the sample at time intervals behind the excitation spots. Light passing through each aperture is dispersed into its component wavelengths and imaged onto spectral bins arranged in rectangles on a CCD, wherein the rectangles are orthogonally oriented to the confocal slit. In certain embodiments, separate CCDs are used to image the light coming through each confocal aperture; hence, a three-slit configuration would require three CCDs. In other embodiments, a single CCD is used to image the light from all of the apertures. The CCD in this embodiment would be configured to provide a matrix of rectangles; each aperture is imaged onto a particular row (or column) of rectangles on the CCD. Thus, a single CCD provides data on the position, time-resolution, and spectrum of each fluoresence emission event.

What is claimed is:

1. A confocal scanning system comprising:

an excitation energy delivery system to direct energy toward a first region of a sample;

an optical detection system for measuring fluorescence of the sample induced by the energy;

a spatial filer disposed optically between the sample and the optical detection system to limit the measured fluorescence to at least one second region of the sample; and a mechanism coupling the energy delivery system and the spatial filter to the sample so that the first and second regions scan the sample sequentially.

2. The system of claim 1 wherein the mechanism scans the first and second regions at a speed and with a distance therebetween so that the fluorescence is measured a predetermined time after the energy.

3. The system of claim 1 further comprising a plurality of spatial filters, the spatial filters comprising pinhole apertures aligned so that the fluorescence is measured at a plurality of times after the energy.

4. The system of claim 1 wherein the energy comprises laser energy.

* * * * *